United States Patent [19]

Saito et al.

[11] 4,082,786

[45] Apr. 4, 1978

[54] PROCESS OF PRODUCTION OF AROMATIC NITRILES

[75] Inventors: Masao Saito; Mamoru Onozawa; Kaoru Sasagawa; Takamasa Kawakami, all of Niigata, Japan

[73] Assignee: Mitsubishi Gas Chemical Company, Inc., Tokyo, Japan

[21] Appl. No.: 741,114

[22] Filed: Nov. 11, 1976

[30] Foreign Application Priority Data

Dec. 16, 1975 Japan .............................. 50-149884

[51] Int. Cl.$^2$ .......................................... C07C 120/14
[52] U.S. Cl. .............................. 260/465 C; 252/432; 252/467
[58] Field of Search .................................. 260/465 C

[56] References Cited

U.S. PATENT DOCUMENTS

| | | |
|---|---|---|
| 3,230,246 | 1/1966 | Callahan et al. .............. 260/465.3 |
| 3,472,892 | 10/1969 | Callahan et al. .............. 260/465.3 |
| 3,501,517 | 3/1970 | Hughes et al. ................ 260/465 C |
| 3,772,212 | 11/1973 | Saito et al. .................. 260/465 C X |

*Primary Examiner*—Dolph H. Torrence
*Attorney, Agent, or Firm*—Armstrong, Nikaido, Marmelstein & Kubovcik

[57] ABSTRACT

Aromatic nitriles can be produced at a high conversion and at a high selectivity by filling cylindrical wire netting into a fluidized bed reactor when the aromatic nitriles are produced by subjecting a mixture of an aromatic hydrocarbon, ammonia and molecular oxygen to fluid catalytic reaction in the presence of a fluid catalyst.

15 Claims, No Drawings

PROCESS OF PRODUCTION OF AROMATIC NITRILES

The present invention relates to a process for producing aromatic nitriles by subjecting a mixture of an aromatic hydrocarbon, ammonia and molecular oxygen to catalytic reaction in a fluidized bed.

Fluidized-bed reaction process have advantages over fixed-bed reaction process in that the transfer velocity of heat or materials is high and temperature distribution in the reactor is uniform. In fluidized-bed reaction process, however, contact of the gas with catalyst particles is unstable and is greatly affected by the diameter of the fluidized bed apparatus, the structure of a gas distributor, the height of the fluidized bed, the flow rate of the gas, the particle size, size distribution and density of the fluidized particles, etc. As a result, the reaction gas gives rise to bubbling or channelling and contact thereof with catalyst particles becomes poor. Thus, operation becomes very difficult and the conversion is lowered. As a means for improving contact of the gas with catalyst particles by obviating such defects of the fluidized bed and preventing the growth of aggregation of bubbles in the bed, a method which comprises filling packings such as Raschig ring, etc. into the fluidized bed reactor is known. When this method is applied to the ammoxidation reaction of aromatic hydrocarbons, however, it is impossible to increase the flow rate of the gas and no satisfactory results can be obtained. The present inventors have now found that cylindrical wire netting can be used as an excellent packing suitable for such a reaction.

According to the present invention, there is provided an improved process for producing aromatic nitriles which comprises subjecting a mixture of an aromatic hydrocarbon, ammonia and molecular oxygen to fluid catalytic reaction in the presence of a fluid catalyst, characterized by filling cylindrical wire netting (wire netting rings) into a fluidized bed reactor.

The cylindrical wire netting (wire netting rings) which may be used in the present invention vary in size according to the size and shape of a reactor, the flow rate of the gas, the particle size of the catalyst, etc., but are cylindrical wire netting having a diameter of 5 to 100 mm, and preferably 10 to 100 mm, and a length of 5 to 300 mm, and preferably 10 to 200 mm. The opening of these wire netting rings is 1.0 mm to 30 mm, and preferably 2.0 to 10 mm. If the opening is less than 1.0 mm, the fluidization of the catalyst is obstructed. Also, if the opening is more than 30 mm, the filling effect becomes lower. Also, the diameter of the wire used in the wire netting rings is not particularly limited, but may be such one as gives a strength enough to prevent deformation on use. Thus, the diameter of the wire may be 0.4 mm or more. The amount of the wire netting rings filled may be such an amount as fills up the whole volume occupied by the catalyst under the operating conditions, but is 30% by volume or more, and preferably 50% by volume or more, based on the volume occupied by the catalyst under the operating conditions.

The starting aromatic hydrocarbons which can be converted into aromatic nitriles according to the process of the present invention include toluene, ethylbenzene, xylene, diethylbenzene, mesitylene, diisopropylbenzene, cymene, methylnaphthalene, etc.

The concentration of the aromatic hydrocarbon in the reaction gas is 0.5 to 5%, and preferably 0.5 to 4%, by volume when air is used as an oxygen source.

The concentration of ammonia in the reaction gas must be more than the theoretical amount. Although the yield of an aromatic nitrile from an aromatic hydrocarbon slightly increases with an increase in the concentration of ammonia, the concentration is advantageously about 2 to about 10 times as much as the theoretical amount from a viewpoint of the technique of recovery of unreacted ammonia.

Also, it is required that the concentration of oxygen in the reaction gas is at least 1.5 times as much as the theoretical amount, and preferably about 3 to about 50 times as much as the theoretical amount. As an oxygen source, air is generally used. It is possible to use nitrogen, carbon dioxide, steam, etc. as an inert diluent.

The reaction may be carried out at a temperature from 300° to 500° C, and preferably 330° to 450° C. At a temperature of less than 300° C, the conversion of the starting aromatic hydrocarbon is low. Also, at a temperature of more than 500° C, the amounts of carbon dioxide, hydrogen cyanide, etc. formed increase and the yield of the aromatic nitriles decreases. The reaction temperature at which the highest yield of the aromatic nitriles can be obtained varies slightly according to the kind and concentration of the aromatic hydrocarbon and contact time, etc. Therefore, it is preferable that the reaction temperature is suitably selected from the above-mentioned range.

The contact time of the reaction gas and the catalyst may generally vary within a considerably wide range, but is preferably 0.5 to about 30 seconds. Accordingly, the space velocity is preferably 1,500 hr$^{-1}$ or less. If the space velocity exceeds 1,500 hr$^{-1}$, the contact efficiency is reduced and the recovery of the catalyst becomes difficult, rendering the operation practically disadvantageous. The linear velocity is preferably 10 to 80 cm/sec (90% or less of the particle carrying velocity).

The catalysts containing vanadium and chromium as their catalyst component are preferably used in the present invention. Particularly preferable is a catalyst having an atomic ratio of vanadium — chromium — boron of V : Cr : B = 1 : 0.5 - 2 : 0.1 - 1.2 in which oxides of these elements have been supported on silica in an amount of 30 to 60% by weight. Here, the atomic ratio is particularly preferably 1 : 0.7 - 1.5 : 0.3 - 1.0. The state of the respective oxides in the catalysts is not necessarily fixed. The amount of the oxides of the elements supported on silica in the catalysts is expressed as % by weight of the total oxides in the catalyst as calculated as $V_2O_5$, $Cr_2O_3$ and $B_2O_3$, respectively. These catalysts can be produced according to the process described in British patent specification No. 1,351,523.

The particle size of the catalysts is 10 to 200 μ, and preferably 10 to 150 μ.

According to the present invention, a reduction in the contact efficiency of the reaction gas and the catalyst due to the blowing through of the gas, back mixing, etc. can be prevented. It is effective in increasing the conversion and improving the selectivity.

The following examples illustrate the present invention.

EXAMPLE 1

Into a stainless steel fluidized bed reactor having a diameter of 83 mm and a length of 2500 mm and equipped with a gas distributor of a sintered metal at its tower bottom and a catalyst recovery apparatus at its tower top, which might be cooled outwardly, were filled irregularly 10 of wire netting rings made of a 10 mesh stainless steel wire netting (the diameter of the wire 0.5 mm, the opening of the rings 2.0 mm, the diameter of the rings 20 mm, the length of the rings 20 mm). The catalyst used was a vanadiumchromium-boron supported on silica catalyst having a particle size of 10 to 100 $\mu$ and an average particle size of 60 $\mu$ which had been prepared according to the process described in British patent specification No. 1,351,523. 6.5 Liters of the catalyst was filled. Through the lower part of the reactor were charged 2,300 l/hr of air, 350 l/hr of ammonia and 230 g/hr of m-xylene (space velocity 415 hr$^{-1}$). The reaction was carried out at 400° C. Thus, isophthalonitrile, metatolunitrile and metacyanobenzamide were obtained in yields of 83.0% by mole, 0.7% by mole and 1.5% by mole, respectively, based on the m-xylene charged.

COMPARATIVE EXAMPLE 1

The reaction was carried out under the same conditions as in Example 1 except that no wire netting rings were used. Thus, isophthalonitrile, metatolunitrile and metacyanobenzamide were obtained in yields of 68.8% by mole, 3.4% by mole and 7.0% by mole, respectively, based on the m-xylene charged.

EXAMPLE 2

10 Liters of wire netting rings made of a 10 mesh stainless steel wire netting (the diameter of the wire 0.5 mm, the opening of the rings 2.0 mm, the diameter of the rings 30 mm, the length of the rings 30 mm) were filled into the reactor of Example 1. The reaction was carried out under the same conditions as in Example 1. Thus, isophthalonitrile, metatolunitrile and metacyanobenzamide were obtained in yields of 81.0% by mole, 0.6% by mole and 3.0% by mole, respectively, based on the m-xylene charged.

EXAMPLE 3

10 Liters of wire netting rings made of a 6 mesh stainless steel wire netting (the diameter of the wire 0.8 mm, the opening of the rings 3.4 mm, the diameter of the rings 30 mm, the length of the rings 30 mm) were filled into the reactor of Example 1 in place of the 10 mesh rings in Example 1, and the reaction was carried out under the same conditions as in Example 1. Thus, isophthalonitrile, metatolunitrile and metacyanobenzamide were obtained in yields of 80.7% by mole, 1.1% by mole and 3.1% by mole, respectively, based on the m-xylene charged.

EXAMPLE 4

5 Liters of the same wire netting rings as those used in Example 1 were filled into the reactor of Example 1, and the reaction was carried out under the same conditions as in Example 1. Thus, isophthalonitrile, metatolunitrile and metacyanobenzamide were obtained in yields of 75.2% by mole, 2.6% by mole and 5.6% by mole, respectively, based on the m-xylene charged.

EXAMPLE 5 p-Xylene was used as a raw material in place of m-xylene in Example 1, and the reaction was carried out under the same conditions as in Example 1 in the presence of the same wire netting rings as those used in Example 1. Thus, terephthalonitrile, paratolunitrile and paracyanobenzamide were obtained in yields of 83.4% by mole, 0.5% by mole and 0.7% by mole, respectively, based on the p-xylene charged.

COMPARATIVE EXAMPLE 2

The same reaction as in Example 5 was carried out under the same conditions as in Example 1 except that no wire netting rings were used. Thus, terephthalonitrile, paratolunitrile and paracyanobenzamide were obtained in yields of 75.5% by mole, 3.6% by mole and 2.0% by mole, respectively, based on the p-xylene charged.

EXAMPLE 6

Toluene was used as a raw material in place of m-xylene in Example 1, and 1,500 l/hr of air, 300 l/hr of ammonia and 300 g/hr of toluene were charged into the reactor. The reaction was carried out at 435° C. Thus, benzonitrile was obtained in a yield of 82.0% by mole based on the toluene charged.

COMPARATIVE EXAMPLE 3

The same reaction as in Example 6 was carried out under the same conditions as in Example 1 except that no wire netting rings were used. Thus, benzonitrile was obtained in a yield of 76.5% by mole and the amount of the unreacted toluene recovered was 4.5% by mole based on the toluene charged.

EXAMPLE 7

The same reaction as in Example 1 was carried out at 395° C in the presence of 6.5 l of a vanadium-chromium supported on silica catalyst having a particle size of 10 to 150 $\mu$ and an average particle size of 74 $\mu$. This catalyst had been prepared according to the process as described in Example 1 of U.S. Pat. No. 3,772,212. The other conditions were the same as in Example 1. Thus, isophthalonitrile, metatolunitrile and metacyanobenzamide were obtained in yields of 71.5% by mole, 1.4% by mole and 1.5% by mole, respectively, based on the m-xylene charged.

COMPARATIVE EXAMPLE 4

The same reaction as in Example 7 was carried out under the same conditions as in Example 7 except that no wire netting rings were used. Thus, isophthalonitrile, metatolunitrile and metacyanobenzamide were obtained in yields of 62.7% by mole, 2.8% by mole and 1.9% by mole, respectively, based on the m-xylene charged.

EXAMPLE 8

In the procedures of Example 1, 1,600 l/hr or air, 350 l/hr of ammonia, 230 g/hr of m-xylene and 700 l/hr of nitrogen were charged into the reactor and the reaction was carried out at 400° C. Thus, isophthalonitrile, metatolunitrile and metacyanobenzamide were obtained in yields of 83.5% by mole, 1.0% by mole and 1.6% by mole, respectively, based on the m-xylene charged.

What is claimed is:

1. In a process for producing aromatic nitriles by subjecting a mixture of an aromatic hydrocarbon, ammonia and molecular oxygen to fluid catalytic reaction in the presence of a fluid catalyst, the improvement characterized by filling cylindrical wire netting (wire netting rings) into a fluidized bed reactor.

2. The process according to claim 1, wherein said cylindrical wire netting has a diameter of 5 to 100 mm, a length of 5 to 300 mm and an opening of 1.0 mm of 30 mm.

3. The process according to claim 1, wherein the diameter of the wire of said wire netting is at least 0.4 mm.

4. The process according to claim 1, wherein the amount of said cylindrical wire netting filled is 30 to 100% of the volume occupied by the catalyst under the operating conditions.

5. The process according to claim 1, wherein said aromatic hydrocarbon is selected from toluene, ethylbenzene, xylene, diethylbenzene, mesitylene, diisopropylbenzene, cymene and methylnaphthalene.

6. The process according to claim 1, wherein the concentration of said aromatic hydrocarbon in the reaction gas is 0.5 to 5% by volume.

7. The process according to claim 1, wherein the concentration of ammonia in the reaction gas is at least the theoretical amount, and preferably 2 to 10 times as much as the theoretical amount.

8. The process according to claim 1, wherein the concentration of oxygen in the reaction gas is at least 1.5 times, and preferably 3 to 50 times, as much as the theoretical amount.

9. The process according to claim 1, wherein the reaction is carried out in the presence of an inert diluent such as nitrogen, carbon dioxide or steam.

10. The process according to claim 1, wherein the reaction is carried out at 300° to 500° C.

11. The process according to claim 1, wherein the contact time of the reaction gas and the catalyst is 0.5 to 30 seconds, the space velocity is 1,500 hr$^{-1}$ or less, and the linear velocity of the gas is 10 to 80 cm/sec.

12. The process according to claim 1, wherein said fluid catalyst contains vanadium and chromium as its catalyst component.

13. The process according to claim 1, wherein said fluid catalyst contains vanadium, chromium and boron as its catalyst component.

14. The process according to claim 13, wherein the atomic ratio or vanadium : chromium : boron is 1 : 0.5 - 2 : 0.1 - 1.2, vanadium, chromium and boron oxides being supported on silica in an amount of 30 to 60% by weight.

15. The process according to claim 1, wherein said fluid catalyst has a particle size of 10 to 200 $\mu$, and preferably 10 to 150 $\mu$.

* * * * *